(12) United States Patent
Schnell et al.

(10) Patent No.: US 10,046,102 B2
(45) Date of Patent: Aug. 14, 2018

(54) DIAPHRAGM PRESSURE POD FOR MEDICAL FLUIDS

(71) Applicant: NxStage Medical, Inc., Lawrence, MA (US)

(72) Inventors: William J. Schnell, Libertyville, IL (US); David Bell, Grayslake, IL (US); Karen Wilson, Seattle, WA (US); David S. Utterberg, Seattle, WA (US)

(73) Assignee: NXSTAGE MEDICAL, INC., Lawrence, MA (US)

( * ) Notice: Subject to any disclaimer, the term of this patent is extended or adjusted under 35 U.S.C. 154(b) by 108 days.

(21) Appl. No.: 15/195,558

(22) Filed: Jun. 28, 2016

(65) Prior Publication Data

US 2016/0303306 A1    Oct. 20, 2016

Related U.S. Application Data

(63) Continuation of application No. 13/928,454, filed on Jun. 27, 2013, now Pat. No. 9,393,397, which is a
(Continued)

(51) Int. Cl.
*G01L 7/08* (2006.01)
*A61M 1/36* (2006.01)
(Continued)

(52) U.S. Cl.
CPC ............ *A61M 1/3641* (2014.02); *A61M 1/16* (2013.01); *A61M 1/3627* (2013.01);
(Continued)

(58) Field of Classification Search
CPC .... A61M 1/3641; A61M 1/16; A61M 1/3627; A61M 1/3639; A61M 1/3653; A61M 1/3655; A61M 39/00; F16L 29/005
(Continued)

(56) References Cited

U.S. PATENT DOCUMENTS 3,418,853 A    12/1968    Curtis
3,713,341 A    1/1973    Madsen et al.
(Continued)

FOREIGN PATENT DOCUMENTS

CN    2522849 Y    11/2002
EP    330891 B1    11/1992
(Continued)

OTHER PUBLICATIONS

Decision by Patent Trial and Appeal Board on Case IPR2016-00744, Paper 11, U.S. Pat. No. 8,092,414B2, entered Jul. 28, 2016, pp. 1-19.
(Continued)

*Primary Examiner* — Lisa Caputo
*Assistant Examiner* — Roger Hernandez-Prewit
(74) *Attorney, Agent, or Firm* — Potomac Law Group, PLLC; Mark Catan

(57) ABSTRACT

A tubular medical fluid flow set comprises a pressure sensing chamber connected in flow-through relation to fluid flow tubing of the set. The pressure sensing chamber defines a movable, flexible, impermeable diaphragm dividing the chamber into two separate compartments. The fluid flow tubing communicates with one of the compartments and is isolated from the other of the compartments. A port is carried on the chamber, the port having a seal therein, and communicating with the other of the compartments. Thus, the other of the compartments is hermetically sealed until the port is opened for connection with a pressure measuring device, to keep the flexible diaphragm in a desired, initial position prior to opening of the seal.

7 Claims, 7 Drawing Sheets

Related U.S. Application Data continuation of application No. 13/299,868, filed on Nov. 18, 2011, now Pat. No. 8,491,518, which is a continuation of application No. 11/270,080, filed on Nov. 9, 2005, now Pat. No. 8,092,414.

(51) Int. Cl.
  *A61M 39/00* (2006.01)
  *F16L 29/00* (2006.01)
  *A61M 1/16* (2006.01)

(52) U.S. Cl.
  CPC ........ *A61M 1/3639* (2013.01); *A61M 1/3655* (2013.01); *A61M 39/00* (2013.01); *F16L 29/005* (2013.01); *Y10T 137/85978* (2015.04)

(58) Field of Classification Search
  USPC .................................... 73/715; 220/277, 278
  See application file for complete search history.

(56) References Cited

U.S. PATENT DOCUMENTS

| | | | |
|---|---|---|---|
| 3,863,504 A † | 2/1975 | Borsanyi | |
| 4,077,882 A | 3/1978 | Gangemi | |
| 4,140,337 A | 2/1979 | Arcella et al. | |
| 4,189,936 A | 2/1980 | Ellis | |
| 4,226,124 A | 10/1980 | Kersten | |
| 4,303,376 A | 12/1981 | Siekmann | |
| 4,353,368 A * | 10/1982 | Slovak et al. ...... | A61M 1/1656 210/646 |
| 4,398,542 A | 8/1983 | Cunningham et al. | |
| 4,412,916 A † | 11/1983 | Kell | |
| 4,457,749 A | 7/1984 | Bellotti et al. | |
| 4,573,997 A | 3/1986 | Wisman et al. | |
| 4,610,256 A | 9/1986 | Wallace | |
| 4,666,598 A † | 5/1987 | Heath et al. | |
| 4,770,787 A | 9/1988 | Heath et al. | |
| 4,795,440 A | 1/1989 | Young et al. | |
| 4,798,090 A | 1/1989 | Heath et al. | |
| 5,044,401 A | 9/1991 | Giesler et al. | |
| 5,186,431 A | 2/1993 | Tamari | |
| 5,197,192 A | 3/1993 | Wylie et al. | |
| 5,360,395 A | 11/1994 | Utterberg | |
| 5,417,673 A | 5/1995 | Gordon | |
| 5,456,675 A | 10/1995 | Wolbring et al. | |
| 5,554,113 A | 9/1996 | Novak et al. | |
| 5,643,205 A | 7/1997 | Utterberg | |
| 5,693,008 A | 12/1997 | Brugger et al. | |
| 5,722,399 A * | 3/1998 | Chevallet et al. .. | A61M 1/3639 600/485 |
| 5,738,334 A | 4/1998 | Proni | |
| 5,924,584 A | 7/1999 | Hellstrom et al. | |
| 5,980,741 A | 11/1999 | Schnell et al. | |
| 6,014,800 A | 1/2000 | Lee | |
| 6,039,078 A † | 3/2000 | Tamari | |
| 6,280,406 B1 | 8/2001 | Dolecek et al. | |
| 6,409,696 B1 | 6/2002 | Toavs et al. | |
| 6,440,080 B1 | 8/2002 | Booth et al. | |
| 6,517,508 B1 | 2/2003 | Utterberg et al. | |
| 6,526,357 B1 | 2/2003 | Soussan et al. | |
| 6,579,496 B1 | 6/2003 | Fausset et al. | |
| 8,092,414 B2 | 1/2012 | Schnell et al. | |
| 8,491,518 B2 | 7/2013 | Schnell et al. | |
| 2002/0007137 A1 † | 1/2002 | Utterberg et al. | |
| 2002/0049412 A1 | 4/2002 | Madrid et al. | |
| 2002/0177786 A1 | 11/2002 | Balbo | |
| 2004/0068239 A1 | 4/2004 | Utterberg et al. | |
| 2005/0147525 A1 | 7/2005 | Bousquet | |
| 2005/0159710 A1 | 7/2005 | Utterberg | |
| 2005/0209563 A1 | 9/2005 | Hopping et al. | |
| 2005/0224405 A1 | 10/2005 | Neri et al. | |
| 2007/0179422 A1 | 8/2007 | Schnell et al. | |
| 2008/0175719 A1 | 7/2008 | Tracey et al. | |
| 2012/0130338 A1 | 5/2012 | Schnell et al. | |
| 2013/0291970 A1 | 11/2013 | Schnell et al. | |

FOREIGN PATENT DOCUMENTS

| | | | |
|---|---|---|---|
| FR | 2346238 A1 | | 10/1977 |
| JP | 1981-28998 Y2 † | | 7/1981 |
| JP | 1982-169336 A | † | 4/1982 |
| JP | 1984-181162 A | † | 10/1984 |
| JP | 1986-143069 A | † | 6/1986 |
| JP | 61143069 A | | 6/1986 |
| JP | 1986-106252 U | † | 7/1986 |
| JP | 1987-5172 Y2 | † | 2/1987 |
| JP | S625172 Y2 | | 2/1987 |
| JP | S6429267 A | | 1/1989 |
| JP | 1993-23393 A | † | 2/1993 |
| JP | 09024026 A | | 1/1997 |
| JP | H0924026 A | | 1/1997 |
| JP | 2001353215 A | | 12/2001 |
| JP | 2005-95230 A | † | 4/2005 |

OTHER PUBLICATIONS

Decision on Request for Rehearing for Case IPR2016-00744, Paper 13, U.S. Pat. No. 8,092,414B2, entered Sep. 26, 2016, pp. 1-8.
Determination-Reexam Ordered for Reexamination No. 90/013973, U.S. Pat. No. 8,092,414B2, dated Aug. 4, 2017, 13 pages total.
ISO 8638: Cardiovascular Implants and Artificial Organs—Extracorporeal Blood Circuit for Haemodialysers, Haemodiafilters and Haemofilters (Oct. 1, 2004), pp. 1-12.
Kolff et al., "The artificial kidney: a dialyser with a great area", 8 J. Am. Soc. Nephrology (reprinted from CXVII Acta Medica Scandinavica (Jan. 12, 1944) vol. 117(2), pp. 121-134.
Non-Final Office Action for Reexamination No. 90/013973, U.S. Pat. No. 8,092,414B2, dated Dec. 27, 2017, 27 pages total.
Paskalev, "Georg Haas (1886-1971): The forgotten hemodialysis pioneer.", Dialysis and Transplantation, Dec. 1, 2001, vol. 30(12) pp. 828-832.
Patent Owner's Preliminary Response with Exhibits 2001-2008 for Case IPR2016-00744, Paper 9, U.S. Pat. No. 8,092,414B2, submitted Jun. 21, 2016, 129 pages total.
Petition for Inter Partes Review Under 35 U.S.C. §§ 311-319 and 37 C.F.R. § 42.100 et. seq., Case IPR2016-00744, Paper 1, U.S. Pat. No. 8,092,414B2, submitted Mar. 11, 2016, pp. 1-67, with Exhibit 1002 (Declaration of Mr. Charles E. Clemens), pp. 1-113, 180 pages total.
Substantive Portions of File Wrapper History for Reexamination No. 90/013973, U.S. Pat. No. 8,092,414B2, downloaded Jan. 24, 2018, 202 pages total.

\* cited by examiner
† cited by third party

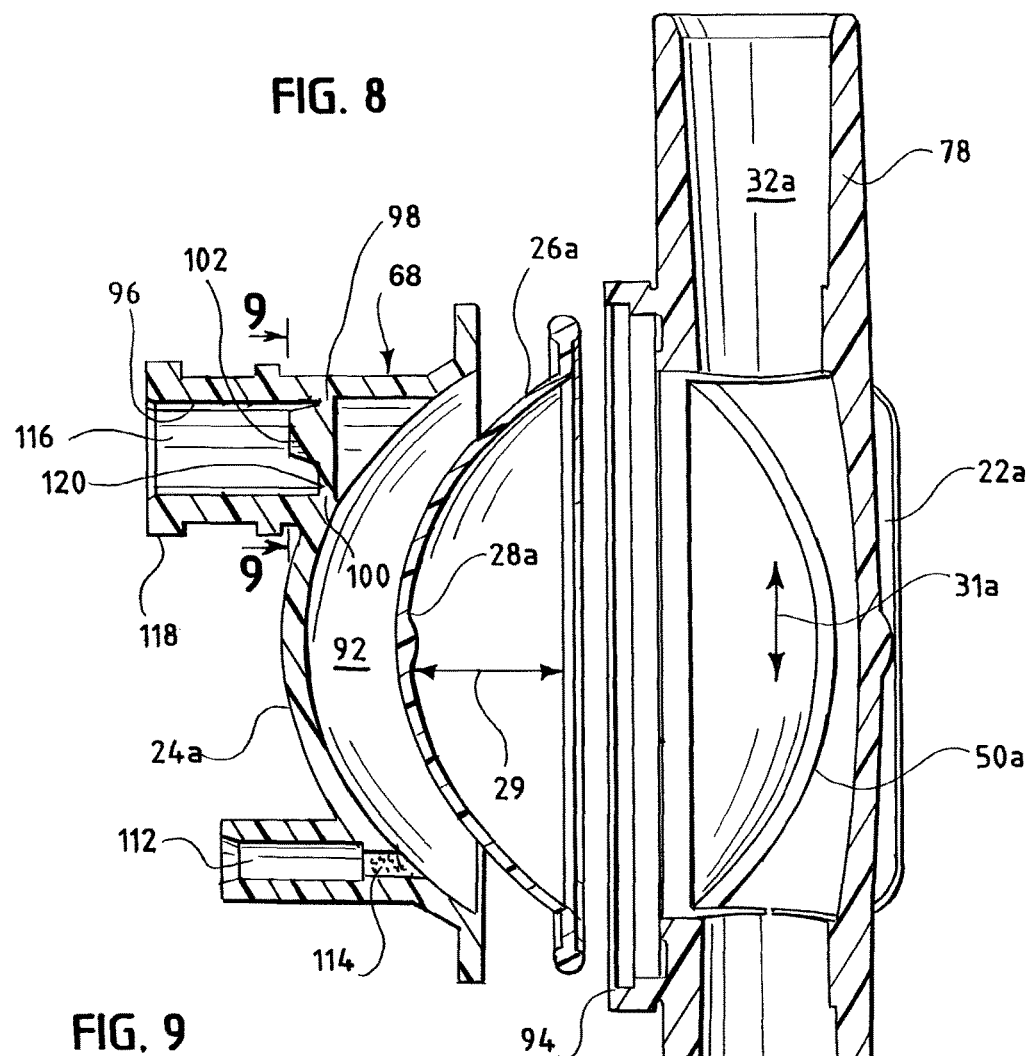
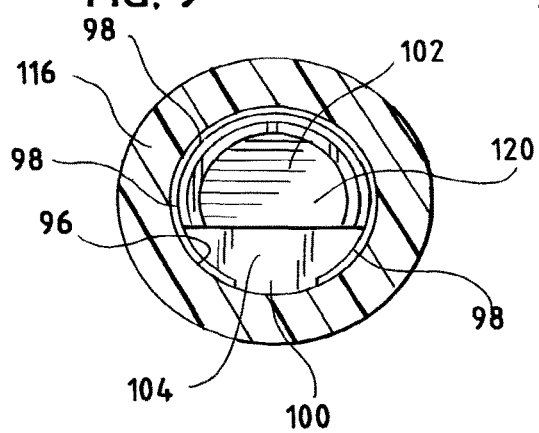

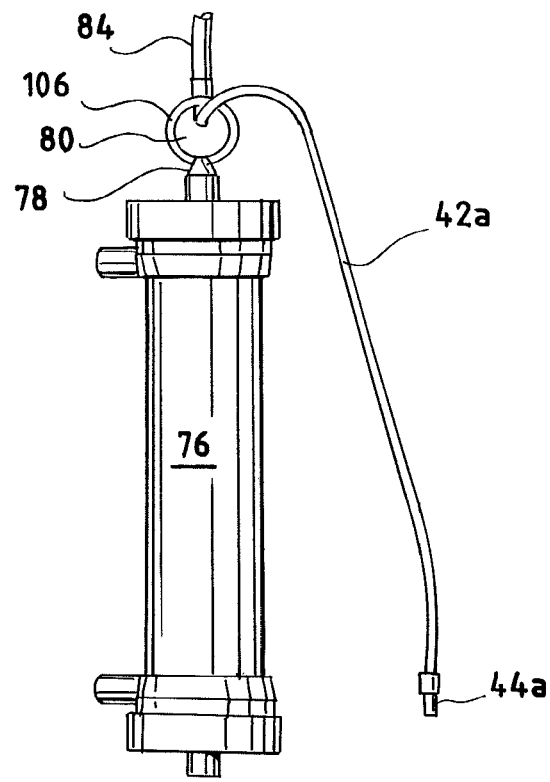
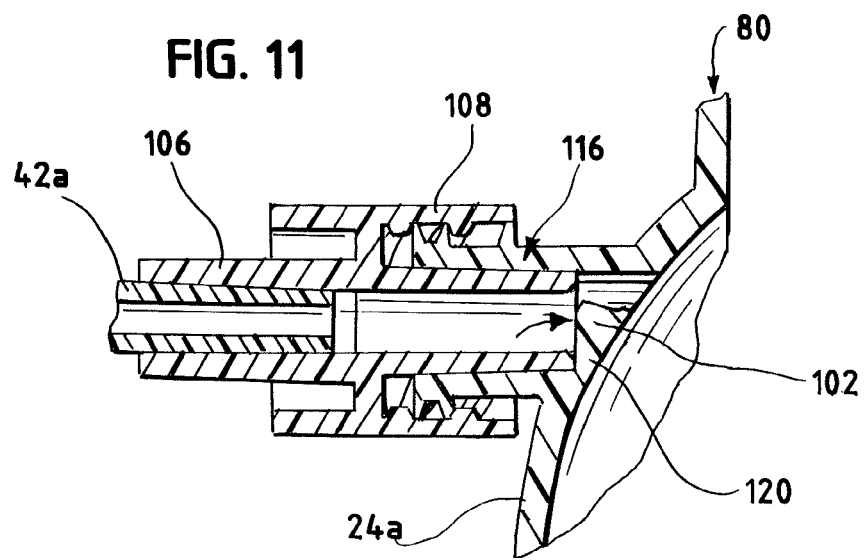

DIAPHRAGM PRESSURE POD FOR MEDICAL FLUIDS

CROSS-REFERENCE TO RELATED APPLICATIONS

The present application is a continuation of U.S. application Ser. No. 13/928,454, filed Jun. 27, 2013, now U.S. Pat. No. 9,393,397, which is a division of U.S. application Ser. No. 13/299,868, filed Nov. 18, 2011, now U.S. Pat. No. 8,491,518, which is a division of U.S. application Ser. No. 11/270,080, filed Nov. 9, 2005, now U.S. Pat. No. 8,092,414, all of which are hereby incorporated by reference herein in their entireties.

BACKGROUND

Sets for extracorporeal blood handling, and also parenteral solution sets, generally require flow-through chambers, often called drip chambers, which, in use, utilize an upper liquid level of the medical liquid passing through it, with an air space on top. Such chambers generally have a permanently connected, branching, hollow-bore, flexible, branch line communicating with said air space for an air pressure line which connects via a reversible connector at its remote end to an equipment pressure port on the permanent equipment, which in turn communicates with a pressure monitor transducer for measuring air-pressure in the chamber as a surrogate for blood-pressure. A pressure-transmitting sterility barrier or diaphragm separates the sterile, disposable set and the unsterile permanent equipment.

These sets generally need to be initially primed with saline or another parenteral solution, where the proper upper liquid level is provided in each drip chamber present. Then, in the field of extracorporeal blood handling such as in hemodialysis, connection may be made with a fistula set or other means of access to the patient's bloodstream, and the saline in the primed set is replaced by blood, which is transferred to and from an extracorporeal blood processing device. These devices may comprise hemodialyzers, hemofilters and other devices for extracting components in the blood and returning the balance to the donor.

Alternately, it is also known for a flow-through chamber to incorporate a diaphragm as the pressure-transmitting sterile barrier which may be in direct contact with blood or another parenteral solution, or may only be in contact with air above the upper liquid level. For example, see Madsen et al. U.S. Pat. No. 3,713,341, Borsanyi U.S. Pat. No. 3,863,504, and Gangemi U.S. Pat. No. 4,077,882.

As taught in Brugger et al. U.S. Pat. No. 5,693,008, a flow-through chamber or "pod" is provided, having a diaphragm that transmits pressure but prevents passage of blood across said diaphragm. The pod comprises a rigid chamber in which said diaphragm is mounted and which further comprises a reversible connector which communicates with an airspace between said connector and the non-sterile side of said diaphragm. Said reversible connector, air space and non-sterile diaphragm side are open to atmosphere prior to medical treatment. To prepare for treatment, the reversible connector is connected directly to the pressure port on the face of the dialysis machine. Thus, a pressure tight system is attained and the machine's pressure transducer can measure pressure in the sterile set's flow-through blood pathway. Flow-through blood tubing must convey blood to and from that pod mounted on the face of the machine.

As a disadvantage of these diaphragmatic systems, the great majority of over 100,000+ dialysis machines which are clinically used at the present time have their pre-pump arterial, post pump arterial and/or venous pressure ports for measuring blood pressure positioned on the face of the machine remote from other sites to which the blood tubing must be routed, such as the to the blood pump, the dialyzer (in the case of hemodialysis), the safety shut-off clamp, etc. Thus there is a disadvantage in the use of this system. It is always desirable to minimize the length of the extracorporeal blood flow path, both for reasons of simple economy, to minimize extracorporeal pressure drop and clottable surface area, as well as to minimize the total extracorporeal blood volume.

It is a further disadvantage of the current diaphragmatic system that the non-sterile side of the diaphragm is open to atmosphere prior to being brought into sealing relation with the equipment's pressure port, and therefore may be displaced prior to use. Such displacement results in pressure measurement errors and/or limited pressure measurements.

It is a disadvantage of sets which fit the great majority of the world's dialysis machines that they have drip chambers and permanently attached branch lines. Such branch lines complicate the sets' construction, packaging and use and are expensive.

By this invention, a generally airless pressure chamber (called a "pod") which contains a diaphragm may be used as a substitute for a pressure monitoring drip chamber regardless of the front panel placement of necessary equipment. By this invention the pod is not connected to the pressure port on the face of a dialysis machine, but is spaced therefrom, and the important function of pressure monitoring still takes place. This achieves numerous advantages when compared with the prior drip chamber. Specifically, in the pod of this invention, it becomes unnecessary to set a liquid level as in many prior art chambers, and a blood-air interface can be completely avoided. At the same time, the chamber of this invention may be significantly smaller than the drip chambers of the prior art, and thus may have a reduced priming volume. Also, the volume of the chamber can be temporarily further reduced by manipulation of the diaphragm, for example during the rinse back step in extracorporeal blood handling procedures such as dialysis, to reduce the amount of solution needed in the rinse back process.

Also by this invention there are achieved important advantages when compared with the pods of the prior art. Compared with the priming volume and tubing costs of extracorporeal circuits using pods of the prior art, this invention saves cost because less large-bore blood tubing, but more small bore air pressure monitoring tubing, is used, the latter not containing blood. Thus it can be of a much finer, and cheaper, gauge than blood tubing, resulting in a net savings of plastic and cost, with less blood volume.

Sets utilizing the pod of this invention are easier to prime and operate, because there is no liquid level needed to be set in a chamber, as in the prior art. The pod of this invention may have branch connections for access to parenteral solutions such as saline or heparin solution, and it also may carry a connected, blood-free pressure monitor line (pressure tubing) for connection to a remote pressure port, for the monitoring of particularly blood pressure in the tubular set which carries the chamber. Cost may be saved in the manufacture and assembly of the set of this invention, since the blood tubing may be shortened, as it does not have to extend to the face of the dialysis machine, while also reducing extracorporeal blood volume (priming volume), as a clinical advantage.

The pod of this invention may be positioned precisely where pressure needs to be determined. For example, to detect line kinks or leaks, the pressure measuring chamber or pod should be upstream of the tubing which may leak or become kinked. Where a dialyzer is remotely monitored from a machine (as is generally the case) the placing of a pressure measuring chamber or pod immediately downstream from it is impossible in the case of drip chambers or prior art pods. As a further advantage, the pressure chamber of this invention does not require a permanently connected pressure monitor line. Rather, it can connect with a reusable pressure monitor line. Thus the set utilizing the chamber is less expensive, and there is an overall saving of cash because many disposable sets may be sequentially used with a single pressure monitor line, if desired.

SUMMARY

In accordance with this invention, a tubular blood flow set is provided which comprises a pressure sensing pod connected in flow-through relation to fluid flow tubing of said set, typically blood tubing. The pressure sensing pod defines a movable, flexible, impermeable diaphragm dividing the pod into two separate compartments. The fluid flow tubing communicates with one of the compartments for fluid flow through the compartment. The fluid flow tubing is isolated from the other of the compartments by the diaphragm. A pod connector carried on the pod communicates with the other of the compartments. In one embodiment of this invention a hollow-bore branch line is permanently attached to and communicates with the pod connector. The branch line is long enough, and terminates in a releasable connector such that it mates with the machine's pressure port. In another embodiment, the pod connector is releasable, and may be temporarily attached to a separate branch line bearing an appropriate mating connector for the pod connector. As before, the branch line is long enough, and terminates in a releasable or non-releasable connector to the pressure sensing machines pressure port. Preferably, the pod connector is sealed prior to attachment to either the machine port directly, or preferably to said separate branch line. Such sealing may be permanently breached, as in a frangible barrier, or it may be reversibly opened such as attained by a slit disc of U.S. Patent Publication No. US 2005/0159710 A1, the disclosures of which are incorporated by reference.

Thus, the one compartment of the pod is part of a fluid flow path, typically blood, through the fluid flow set and the pressure sensing chamber. The other of the compartments is preferably hermetically sealed by a sealed port, until opened for connection with a pressure measuring device. The effect of this is to keep the movable, flexible diaphragm in a desired, initial position prior to said opening. The diaphragm, when the hermetic seal is broken, is capable of moving between a first position and a second, opposed position in which the diaphragm in the first position can bow outwardly from the blood pathway, to maximize blood volume in the chamber, while the diaphragm in the second position can bow inwardly to minimize, but typically not eliminate, blood volume in the chamber. In some embodiments, the diaphragm has a central, domed portion which can flip between the two positions.

In an arterial, pre-pump pod embodiment where the pod is generally subjected to negative pressure [but sometimes positive pressure when priming], the diaphragm may be moveable between the first and second positions when the hermetic seal is broken, but not before. The same holds for the post pump, positive pressure situation.

In some embodiments, the sealed port is opened by engagement with a connector which is carried on an end of a length of separate pressure tubing. This connector may be, for example, a male luer lock connector or any other desired connector that is compatible for connection with the sealed port carried on the pod. Also, the pressure tubing connects at an opposed end thereof with the pressure measuring device, either permanently or separably, as may be desired.

Specifically, in some embodiments the sealed port of the pod may be so sealed by a partition having a peripheral connection with a lumen wall of the sealed port. A major portion of the peripheral connection is relatively thin, capable of being easily broken open, while a minor portion of the peripheral connection is thicker than the major portion of the peripheral connection, so that the minor portion functions as a hinge. Thus the partition can pivot, but it cannot separate from the rest of the sealed port as it is torn open by an advancing connector such as a male luer.

In some embodiments, the sealed port partition is relatively thin in a line of tearing weakness extending across the partition, as well as around most of the periphery so that, when broken, there are two hinges and half partitions which distend a lesser distance inwardly than the previous embodiment.

Further, by this invention in some embodiments, a first section of the partition adjacent to the major portion (but radially inwardly therefrom) is thicker than the corresponding, opposite section of the partition adjacent to the periphery thereof. The effect of this is to focus rupturing force provided by pressure from a male luer or other tubular connector to the periphery of the partition at the first section. Thus, when a normal, flat-ended tubular connector is inserted into the sealed port and pressed inwardly, it encounters the first section and presses against it, without contact with the opposite section. Accordingly, the rupturing force is focused against only a portion of the periphery of the partition, that portion being at least part of the major portion of the peripheral connection, thin enough to be easily broken open. This force is focused because the tubular connector is engaging only the first section of the partition because of its increased thickness, and not the corresponding, opposite section. Thus the total force required for frangibility of the partition is less. The partition easily opens and pivots about the minor portion of the peripheral connection, to open the sealed port.

Typically the first section of the partition is at least twice as thick as the corresponding, opposite section.

Thus, a blunt tube such as a male luer can easily open the partition.

Further in accordance with this invention, a pressure sensing chamber or pod for a tubular medical flow set described above may be directly and permanently attached to an inlet or outlet connector, for direct, typically releasable, connection with an extracorporeal blood processing device. The set that carries the chamber is for handling extracorporeal blood flow, with the pressure sensing chamber being directly attached, preferably to the downstream end of, the extracorporeal blood processing device such as a hemodialyser. The pressure monitor system that utilizes the pressure sensing pod is thus capable of monitoring pressure of the entire length of the blood flow tubing extending downstream from the extracorporeal blood processing device, typically a dialyzer. This is a significant area for pressure monitoring, because it is typically the majority of the extracorporeal blood flow circuit that operates under positive pressure. A serious blood leak or kink anywhere along the line downstream of the dialyser can thus be detected by a pressure fluctuation, if there is constant monitoring through the pressure sensing chamber.

Generally, the diaphragm of the pod occupies substantially a first position when the interior of the flow set is filled with a blood at close to atmospheric pressure, as when the pump is stopped or during priming, and the diaphragm is urged towards the second position whenever the blood side pressure on the diaphragm is less than the air side pressure on the diaphragm. Such greater air side pressure may be intentionally applied through said pressure tubing, which may be flexible, by a machine system having an air pump communicating with said tubing, or the pressure tubing may be disconnected from the machine's port and reconnected to a device such as a syringe. In either case, positive pressure may intentionally be applied to the chamber to drive the diaphragm towards the second position, which may be desirable during a blood rinseback procedure, involving rinsing blood from the tubular set, back to the patient, since the internal volume of the chamber is minimized by such intentional pressurization, thus reducing the hydration that must be provided to the patient. The tubing may carry a clamp or valve to retain the positive pressure at the diaphragm.

Alternately, the pod of this invention may comprise an arterial post-pump and/or venous pod embodiment where the pod is generally subjected to positive pressure. The diaphragm may substantially initially occupy the second position when the interior of the flow set is filled with blood at close to atmospheric pressure; and the diaphragm is urged towards the first position whenever the blood side pressure is greater than the air side pressure on the diaphragm, so that the greater the blood pressure, the more the diaphragm is driven from the second position toward the first position.

Movement of the diaphragm between the first and second positions is restricted by the fact that, in the pressure sensing process, a sealed, fixed volume of air exists between the diaphragm and a pressure sensing transducer, with the branch line pressure tubing extending therebetween. Thus, movement of the diaphragm toward one position or another position will reflect a change of the level of compression of the air or other compressible fluid in the fluid flow path between the diaphragm and the pressure sensing transducer, thus transmitting the pressure of the blood to the transducer. Thus, in this circumstance, the diaphragm does not flip back and forth with ease between the first and second positions because of the sealed volume of air or other compressible fluid in the flow path between the diaphragm and the pressure transducer.

Further in accordance with a preferred embodiment of this invention, the sealed port communicating with the other of the compartments of the pressure sensing chamber facilitates the priming of the medical fluid flow set, since it provides the sealed, fixed volume of air discussed above that holds the diaphragm in the desired position. This desired position may vary, depending on whether the pod is to be exposed to reduced pressure or elevated pressure during normal operation.

One can see that if the other of the compartments separated from fluid flow by the diaphragm is not sealed, the diaphragm will flip from one position to the other in accordance with pressures that are encountered in the fluid (blood) flow path during shipping, installation or priming. If the diaphragm winds up in the wrong position at the end of priming, inconvenient steps will have to be taken, while maintaining sterility, to remedy it.

Thus, the sealed port holds the diaphragm in its desired position, which position depends upon its contemplated use, until priming or other desired step(s) has been completed. Then, one can open the seal of the pressure sensing pod port as a sealed connection is made with a pressure line, so that now the pod is again sealed with the pressure line communicating between the chamber and the pressure monitor.

Specifically, when the blood flow set of this invention is being used as an arterial set for hemodialysis, upstream from the roller pump tubing so as to encounter negatively pressurized blood (i.e., blood under suction pressure from the roller pump), it may be preferred for the pod diaphragm at ambient pressure to initially occupy a position substantially close to the first, volume maximizing position. Thus, as negative (subatmospheric) bloodline pressure increases, the diaphragm moves incrementally toward the second position, with that movement being resisted by the sealed, fixed volume of air, which is being expanded in response to the negative (subatmospheric) pressure of the blood acting upon the diaphragm. Thus, the negative pressure is duplicated in the fixed volume of air or other compressible fluid, and may be sensed by the pressure transducer, which is positioned remotely from the pressure sensing chamber and diaphragm used in this invention. Under positive pressure blood line conditions, the diaphragm starts generally at the opposite, first position. However, when there is open or ambient pressure on both sides of the diaphragm, the diaphragm may flip back and forth between its first and second positions relatively easily.

The above-described chamber or pod may have a bottom wall, which further defines a channel having a wall of U or V-shaped cross section. Accordingly, when the diaphragm is forced into its extreme, second position, fluid flow is not blocked through the channel, so that flow is provided in all circumstances through the medical fluid flow set. Specifically, the channel wall may be U-shaped and substantially contiguous with the internal diameter wall of the flow tubing of the set, preferably being substantially aligned with, and of a size similar to, the inner diameter wall of the flow tubing of the set where it connects with the chamber. This can promote efficient fluid flow through the entire set, even when the diaphragm is held in its second, blood volume minimizing position.

Also, one or more access ports may be provided to the pod's inlet or outlet connection or the pressure chamber communicating with its blood pathway. These ports may be used to provide parenteral solution, heparin, or other medicaments to the blood or for withdrawing blood or air or saline from the flowpath.

The pod may be connected at one end via a flowthrough port with the pump tubing of the set, which comprises typically roller pump tubing, which is carried on many extracorporeal blood transport sets. Alternately, the flowthrough port may connect with another pump apparatus, or it may connect to a venous air-trapping chamber, or any other flowthrough component of an extracorporeal set. The pressure chamber (pod) then has another end with another flowthrough port which may fit tubing of same or different diameter from pump tubing or to another flowthrough component. Thus, this pod may serve the additional function of a pump segment connector, a tube connector, or a device connector, as well as providing other function as described herein.

Further by this invention, blood may be rinsed from the extracorporeal blood flow tubing and returned to the patient, after an extracorporeal blood flow procedure such as hemodialysis. The blood flow tubing is connected to the pod having the flexible diaphragm, which defines a blood holding volume. The diaphragm is sealingly mounted within the chamber. This method comprises the steps of pressurizing the chamber to move the diaphragm, to cause the blood holding volume of the chamber to be substantially minimized, without blocking blood flow through the blood flow tubing and chamber. Then, parenteral solution such as saline is caused to pass into the tube and chamber to replace the blood, while the blood is returned to the patient. The substantially minimized blood holding volume of the chamber reduces the fluid volume of the extracorporeal blood flow tube, which provides clinical advantage, and requires the use of less solution to provide the desired rinseback.

Typically, this method is practiced after the step of using the pod to sense blood pressure in the blood flow tube during extracorporeal blood processing, with the diaphragm being positioned to enlarge the blood-holding volume in the chamber above the minimum volume, a length of pressure tubing extending from the chamber to a pressure monitor device Further by this invention, a pressure transmitting pod defines a chamber, the pod being for connection and flow-through relation to fluid flow tubing of the fluid flow set. The pod has a flexible fluid impermeable diaphragm dividing the pod into separate compartments. The first of the compartments communicates with flow connectors for the fluid flow tubing. A second of the compartments communicates with a pressure connection port for connection with the length of pressure tubing at one end thereof. The tubing is for sealed connection at its other end to a remote pressure connector of a pressure sensing machine, to transmit pressure from the second of the compartments through the pressure tubing to the pressure sensing machine for pressure monitoring. The diaphragm has a dome shape, and is sufficiently flexible to easily distort in a manner reflective of pressure changes, to vary the volumes of the two compartments. In some embodiments, the diaphragm of dome shape can vary the volume of the respective compartments at a pressure variation of 500 mm mercury by at least 3 cc.

The pressure tubing may be permanently connected to the connection port, the pod, or releasably connected as previously described. The pressure tubing at its other end can connect to a remote tubing connector for connection to the machine remote pressure port during medical treatments, or permanently, if desired. As previously described, the pod connection port is sealed from the atmosphere by an internal partition, the seal being openable by sealing attachment with a connector of the pressure tubing.

BRIEF DESCRIPTION OF THE DRAWINGS

In the drawings.

FIG. 8 is an exploded, longitudinal sectional view of a pressure sensing pod of the set of FIG. 7.

FIG. 9 is a sectional view taken along line 9-9 of FIG. 8.

FIG. 10 is a fragmentary, enlarged plan view of a portion of FIG. 7, showing the connection of the pressure sensing pod of FIG. 8.

FIG. 11 is a detailed view of FIG. 8, showing how a connector such as a male luer lock connector can rupture the partition for access to the pressure sensing pod.

DETAILED DESCRIPTION

Figure 1:
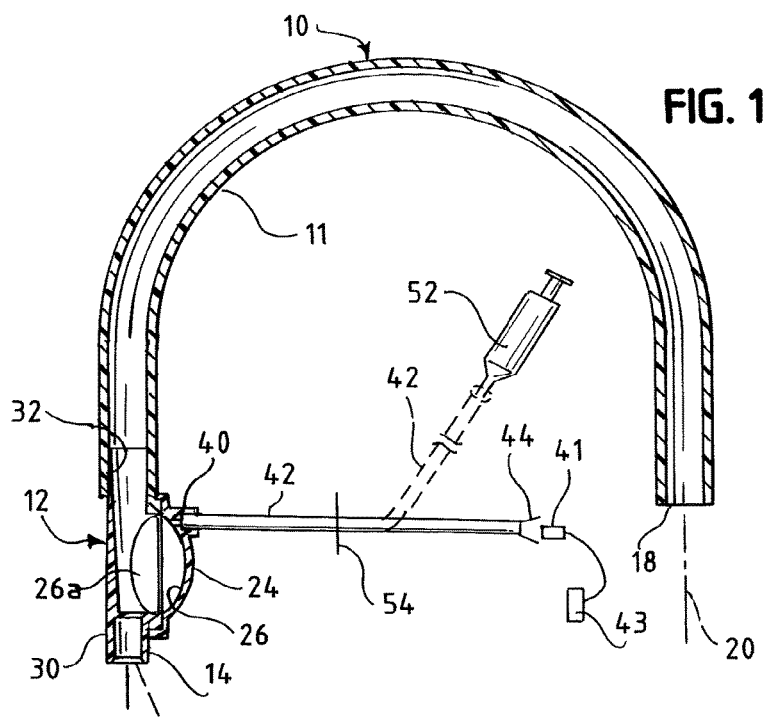
FIG. 1 is a partially diagrammatic, sectional view of a portion of a first embodiment of a tubular blood flow set using the pressure sensing pod and flexible diaphragm disclosed.

Referring to the drawings, FIG. 1 shows a portion of a venous set 10 for hemodialysis, conventional except as otherwise shown. Set 10 is shown to comprise a length of roller pump tubing 11, which is conventionally attached to one end of pressure sensing pod chamber 12 of this invention. The opposed end 14 of pod 12 may connect to a length of set tubing 16, which may connect to other set components, which may be of conventional design for an extracorporeal blood conveying set. Particularly, tubing 16 may fit within the inner diameter of end portion 14 so that such tubing is of a different inner diameter from that of pump tubing 11, if desired. Thus, pressure pod 12 also includes the function of a connector for joining together tubing of differing diameters in the blood set.

Similarly, the end 18 of pump tubing 11 may connect through a conventional connector, such as one shown in U.S. Pat. No. 5,360,395, (the disclosures of which are incorporated by reference) to a length of tubing 20 to connect additional, conventional portions of a tubular blood set for hemodialysis or another extracorporeal blood treatment procedure. For both tubes 20 and 16 these may include injection sites, Y sites, and end connectors, which may connect in this present embodiment respectively with a dialyzer and the patient, but in other embodiments could connect with a different, extracorporeal blood processing device, or any other conventional connection.

Figure 2:
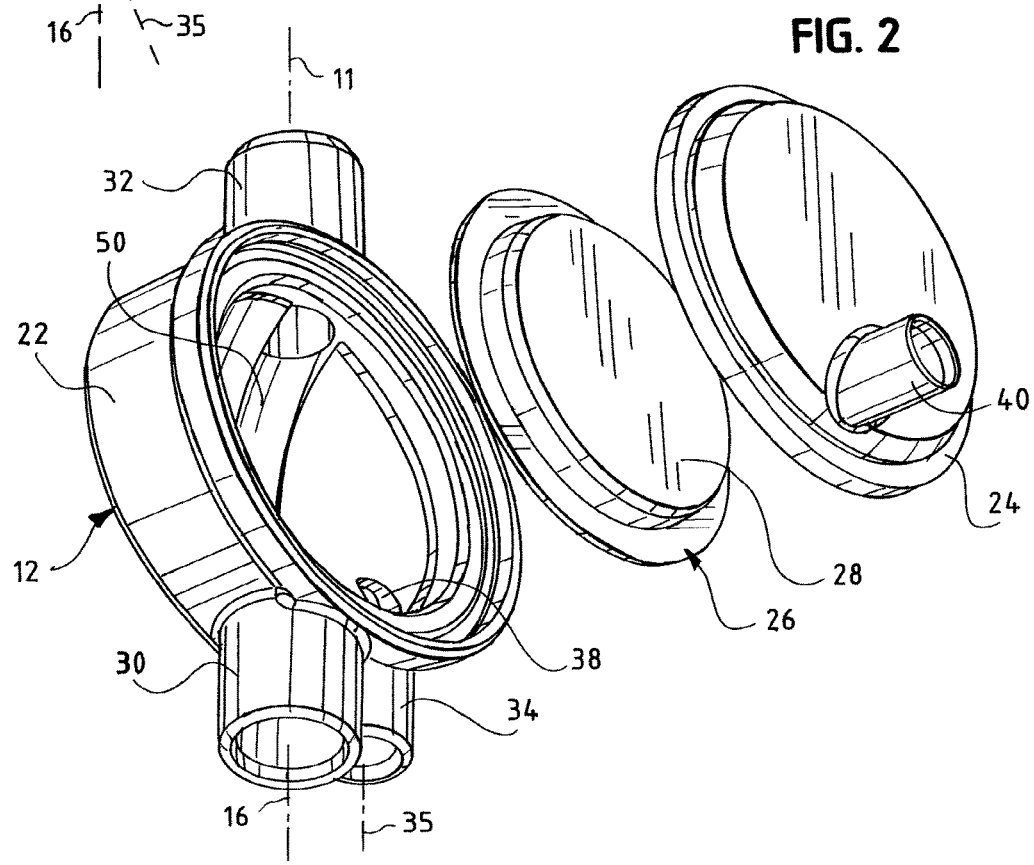
FIG. 2 is an exploded, perspective view of the pressure sensing pod of FIG. 1
Figure 3:
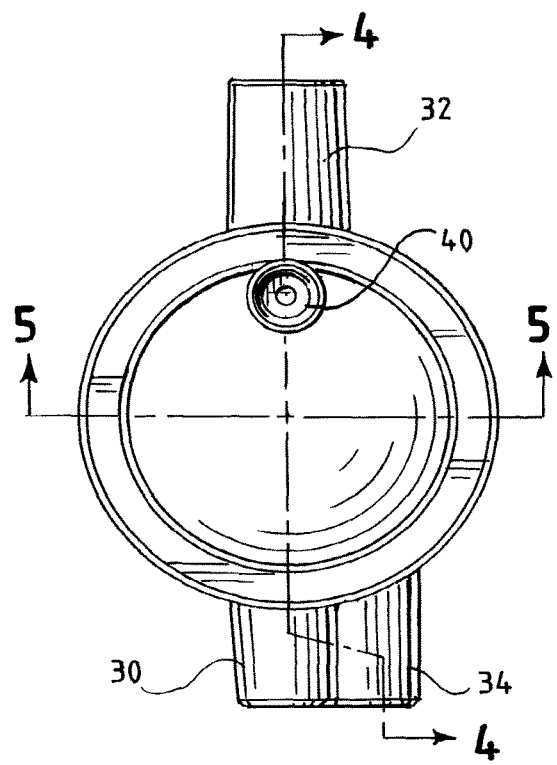
FIG. 3 is a plan view of the pressure sensing pod of FIG. 1.

FIG. 2 shows an exploded view of pressure pod 12, comprising a lower compartment-defining portion 22, an upper compartment-defining portion 24, and a flexible diaphragm 26, which defines a convex, central portion 28 shown to be bulging outwardly from the blood flow portion of the chamber. Compartment defining portion 22 defines a blood inlet port 30 and a blood outlet port 32, as well as an access port 34, which communicates with the interior of the chamber. Each of these ports 30, 32, 34 may be connected to flexible tubing in a conventional manner. As shown in FIG. 1, ports 30, 32 connect with blood flow tubing, while port 34 can connect with tubing 35 which, in turn, may connect with a source of parenteral solution such as saline, or a source of heparin solution, or any other desired or conventional use. Tubing 35 connects with the interior of pressure pod 12 through aperture 38.

The three components 22, 24, 26 of pressure pod 12 seal together with peripheral, circumferential connection, and may be conventionally bonded together by conventional means such as ultrasound sealing or solvent bonding, the components being made typically of conventional thermoplastic and/or thermoset materials, to form the completed chamber as shown in FIGS. 3 to 6. Upper compartment-defining portion 24 as shown in FIG. 2 may be rotated by 180 degrees to form the assembled device shown in FIGS. 1, 3 and 4.

Thus, flexible diaphragm 26 is shown in the assembled pod 12 as being sealingly mounted within a pressure sensing pod between connections of the blood flow tubing 30, 32 and a connection port 40, which may have a seal such as a known valve, or a frangible barrier. Port 40 may connect with a length of pressure tubing 42 (FIG. 1), which is thus connected with the interior of upper compartment-defining portion 24 of pressure sensing pod 12. In FIG. 1, diaphragm 26 is shown to be occupying its first position as previously described, where diaphragm 26 initially bows outwardly to maximize the chamber volume communicating with the blood flow tubing 11, 16. When the blood flow within pod 12 is under negative or subatmospheric pressure, as is the case for portions of set 10 which are upstream of roller pump tubing 11, a suction is induced on diaphragm 26, causing it to be urged downwardly toward inlet and outlet ports 30, 32 in position 26a. Pressure tubing 42 is long enough so that it will reach pressure measuring equipment connector 41 mounted anywhere on the equipment. Equipment pressure connector 41 communicates with a pressure transducer 43 as in a conventional hemodialysis machine, for example, communicating by the joined end connector 44 of tube 42 and connector 41 with the air space within tube 42 and above diaphragm 26. This air space can be sealed when connectors 44 and 41 are joined, so that air neither is added to nor escapes from the volume of air present.

Thus, as suction from the negatively pressurized blood below diaphragm 26 is exerted, an expansion of the fixed volume of air described above takes place, which will allow diaphragm 26 to move downwardly until the negative (subatmospheric) pressures on both sides of the diaphragm are balanced. Thus, the air pressure in tube 42 will match the pressure of the blood below diaphragm 26, and that air pressure can be sensed by pressure sensor 43, and reported by an appropriate signal on preferably a moment-by-moment, real time basis, as is important in the field of extracorporeal blood handling.

Figure 4:
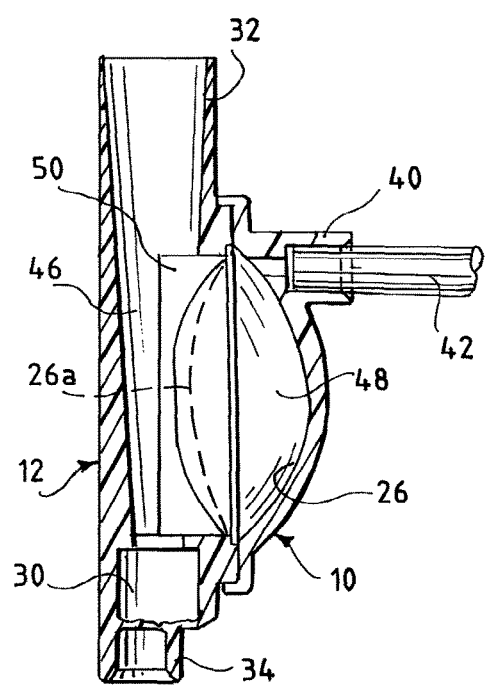
FIG. 4 is a longitudinal sectional view taken along line 4-4 of FIG. 3.
Figure 6:
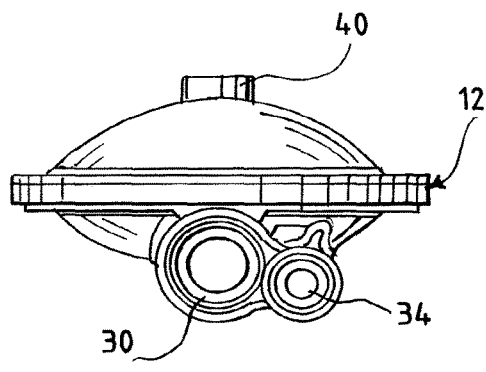
FIG. 6 is an end elevational view of the chamber of FIG. 3.
Figure 5:
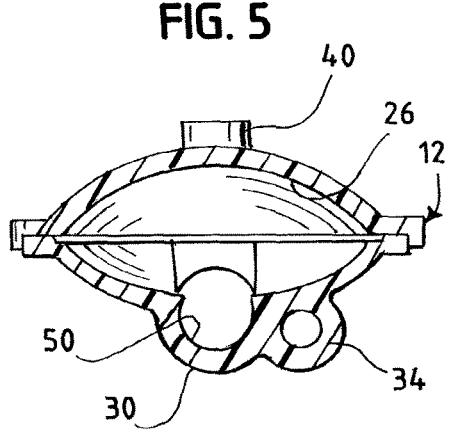
FIG. 5 is a transverse, sectional view taken along line 5-5 of FIG. 3.
Figure 7:
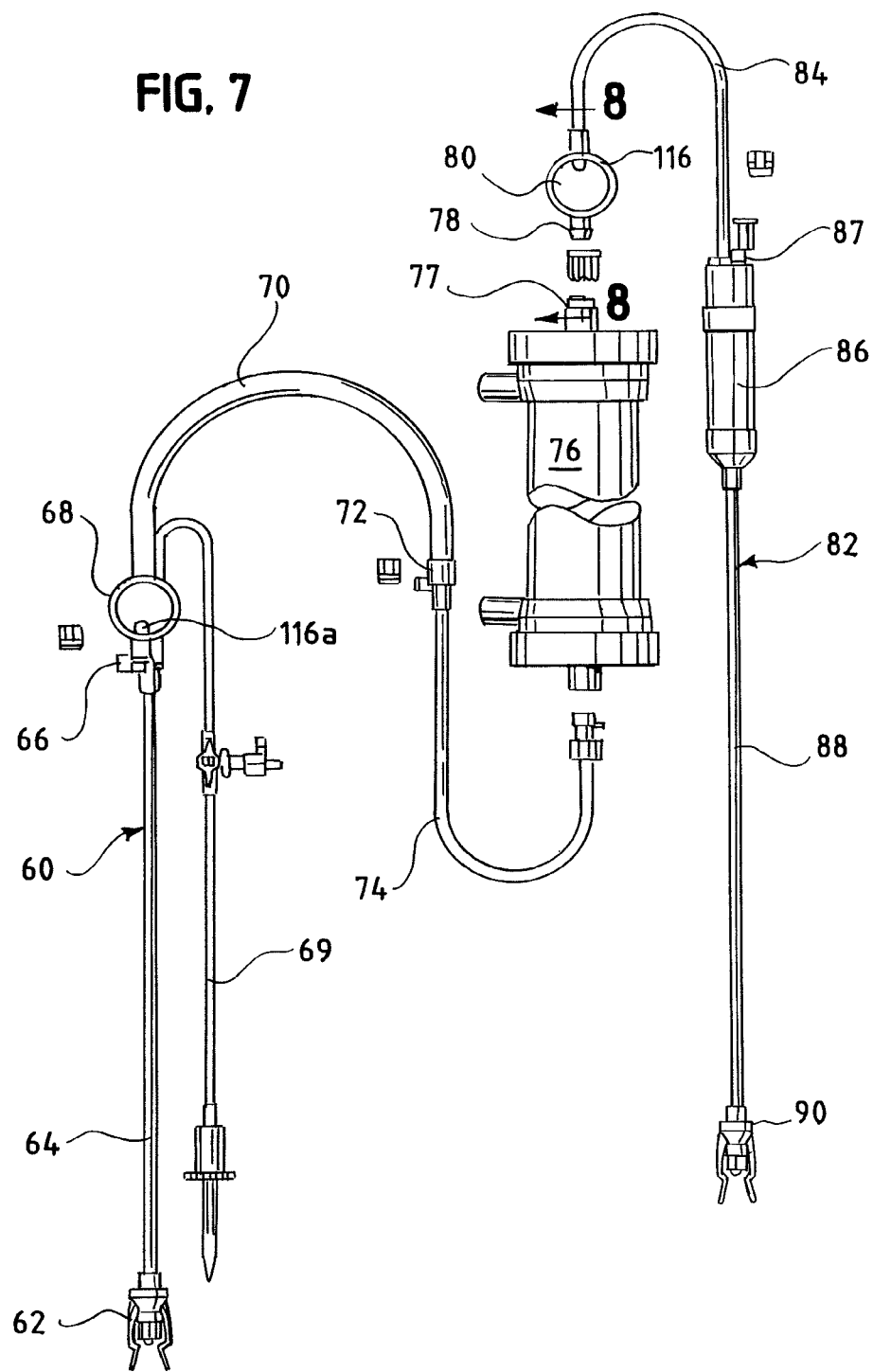
FIG. 7 is a plan view of a hemodialysis set, making use of another embodiment of this invention.

FIG. 4 shows how diaphragm 26 can be moved to its second position 26a, in which it bows inwardly with respect to the blood flow path, to significantly reduce the blood volume in chamber 10. Diaphragm 26 may be initially held in this position for the measurement of positive, superatmospheric pressures in the blood flow path 46, where increases in pressure urge diaphragm 28 outwardly from near the second position 26a (FIG. 4) toward the first position 26 (FIG. 1). However, as before, this movement is resisted by the fact that there is a constant amount of air the space 48 above diaphragm 26 and in pressure tube 42. The air pressure in pressure tube 42 equals the blood pressure in flow path portion 46, with diaphragm 26 moving to make it so, so that the blood pressure can be monitored by transducer 43 while the unsterile pressure connectors 41, 44 remain remote from any blood, being conventionally carried on the face of a dialysis machine or the like at a position spaced from the arrangement of the roller pump, pump tubing 11, and chamber 12. Because of the presence of pressure tubing 42, which extends to connector 41 and pressure transducer 43, wherever it may be located on or in the dialysis machine, it is possible to shorten the overall length of the blood tubing 16, 11, 20, which is desirable for reasons stated above.

The lower compartment portion 22 of pod 12 has a bottom wall which defines a transverse channel 50, which extends between blood inlet port 30 and blood outlet blood port 32. Channel 50 is shown to be of U-shaped cross-section, being substantially aligned with, and having a size similar to, the inner diameter of the blood flow port 30, 32 and the tubing which they carry, to provide efficient fluid flow, even when diaphragm 26 is in its second position, as shown in FIG. 4 as diaphragm 26a. The presence of channel 50 assures that there will not be major blocking of blood flow when diaphragm 26 is in its second position.

When the extracorporeal blood processing procedure is complete, it is necessary to rinse the blood back to the patient in a step known as "rinse back." To accomplish this, pressure tubing 42 may be disconnected from the pressure monitor transducer 43, and the portion of the set which draws blood from the patient can be removed from the patient. Then, pressure tubing 42 is connected with a conventional syringe 52 (FIG. 1), which is depressed to add air or other fluid to the system to cause diaphragm 26 to assume its second position as shown in FIG. 4 (26a). A slide clamp 54 or other type of clamp then may close off pressure tubing 42, to keep diaphragm 26 under pressure and firmly in its second position 26a during the rinse back process, so that the blood containing volume of pod 12 is minimized. Saline solution or the like flows into the system through an access site such as parenteral solution line 35, to replace blood in the set with saline solution, and to return blood back to the patient through the remaining patient connection. Alternatively or additionally, saline solution may be added to the separated end of the set of set portion 16 for rinseback, to terminate the procedure.

Thus, by one embodiment of this invention, blood pressure in a blood flow tube may be monitored through a length of pressure tubing 42 connecting to a diaphragm pod 12 as described, with the diaphragm being positioned near a first position that essentially maximizes the blood holding volume in the pod, although varying, for example negative, pressures in the chamber can result in differing positions of the diaphragm. Then, at the end of the extracorporeal blood flow procedure, pressure sensing pod 12 may be pressurized to move diaphragm 26 to its second position 26a, to cause the blood holding volume of the pod to be substantially minimized, without blocking flow through the blood flow tube and pod. Parenteral solution such as saline is then passed into the tube and pod to replace the blood, while the blood is returned to the patient.

Referring to FIGS. 7-11, another embodiment of the invention is shown for an extracorporeal system for hemodialysis.

Arterial set 60, for removing blood from the patient, comprises a connector 62 for connection with a patient fistula. A length of flexible tubing 64 communicates with an injection site 66 which, in turn, is directly connected to a pressure sensing pod 68, similar to that shown in FIG. 8. Pressure sensing pod 68 connects with pump tubing 70, having a larger diameter than tubing 64. Tubing 70, in turn connects with a connector 72 for connection with lesser diameter blood flow tubing 74, which, in turn, connects with dialyzer 76. The dialysis solution flow lines are eliminated for clarity of disclosure. Solution line 69 connects with pod 68 in a manner similar to line 35 of FIG. 2.

Dialyzer 76, in turn, connects directly to a connector 78, of conventional design, which, in turn, connects directly to another pressure sensing pod 80 of a type disclosed in FIG. 8 and other drawings. Thus, pressure sensing pod 80 can be disconnected from dialyzer 76 to permit reuse of dialyzer 76, coupled with disposability for pressure sensing pod 80 and the connected venous set 82.

Connector 78 may be an appropriate threaded, locking connector or the like, preferably one that meets the DIN specifications or any other means for a secure connection, including an adhesively bonded connection, to dialyzer 76 via its conventional connector 77.

Pressure sensing pod 80 connects with blood flow tubing 84 which, in turn, connects with an air trap chamber 86 which may be conventional, for example of a design similar to that disclosed in U.S. Pat. No. 6,517,508, the disclosures of which are incorporated by reference, in which bubbles are separated by centrifugal flow without suction of the bubbles downwardly by the formation of a vortex. Preferably, air trap chamber 86 may be operated with no upper liquid level or airspace for a completely airless extracorporeal system, but for bubbles collected. Tubing 88 connects to the bottom of air trap chamber 86 at one end, and connects to a conventional patient fistula connector 90. Connector port 87 is also provided.

Turning to FIG. 8, an exploded view of pressure sensing pod 80 is shown, the structure of pressure sensing pod 68 being also similar to it, except for the elements to which it is connected.

Pressure sensing pod 80 defines a lower compartment portion 22a, generally similar to the embodiment shown in FIG. 2, including the bottom flow groove 50a similar to groove 50. Diaphragm 26a is generally of similar design to diaphragm 26, having a bulge 28a of slightly different design. Pressure sensing pod 80 is then closed with upper compartment portion 24a, the peripheries of the portions being sealed together in a conventional manner.

Port 112 may be used for testing in manufacturing, and may be sealed with an amount of sealant 114.

Pressure sensing pod 80 carries sealed port 116, which may be generally of the design of a female luer lock connector, having lugs or screw threads 118 in conventional manner, or other sealing and/or locking means. Port 116 is sealed by partition 120, so that the volume 92, which is spaced by diaphragm 28a from flow ports 30a, 32a, is hermetically sealed when the periphery 94 of pressure sensing pod 80 is sealed. Partition 120 has a peripheral connection with lumen wall 96 of sealed port 116.

The pressure sensing diaphragm in pod 80 defines a dome 28a which has a maximum depth 29 of about 6-7 mm (such as 6.3 mm), and a width of the chamber defined by the dome of about 23-25 mm., specifically 24 mm.

As shown particularly in FIG. 9, partition 120 has a 360° peripheral connection with lumen wall 96, with a major portion 98 of the peripheral connection being relatively thin, typically a film of sealing material about 0.2 to 0.4 mm thick. This thin, frangible peripheral band 98 comprises the major portion of the circumference of partition 120, for example extending from about 270°-330° of the circumference, specifically about 300°.

At the periphery of the remaining portion of the circumference of partition 120, a minor portion 100 of the peripheral connection may be thicker, on the order of 1 mm thick, so that it is not frangible but, rather, serves as a hinge to permit partition 120 to pivot as it is broken open by the pressure of an advancing tubular member, such as a male luer lock connector, advancing through lumen wall 96 of connector 116.

Additionally, as shown in FIGS. 8 and 9, a first section 102 of partition 120 is positioned adjacent to at least some of the major, thin, peripheral portion 98. This first section 102 is thicker than the corresponding, opposite section 104 of partition 120 adjacent to the periphery of minor portion 100. Thus, when a tubular connector 106, as shown in FIG. 11, is advanced into the lumen of connector 116, in the normal circumstance when tubular male luer lock connector 106 has a flush, tubular end, it engages first, thickened portion 102 of partition 120, which is positioned adjacent to major, peripheral portion 98, to focus rupturing force to at least some of major peripheral portion 98. Thus, inward pressure of tubular connector 106 causes rupturing force that is focused onto at least a portion of the thin, major, peripheral portion 98, causing major portion 98 to rip open. Minor peripheral portion 100, however, is thick enough, typically on the order of 1 mm, to not rip, but rather to bend as a hinge, to open connector 116. It is accordingly desirable for connector 116 and particularly partition 120 to be made of a material such as polyethylene, which is capable of forming a reliable, strong hinge upon bending at the hinge thickness used.

As shown in FIG. 8, pressure sensing pod 80 is attached to a blood flow connector 78, and thus may be directly, releasably or permanently connected with an extracorporeal blood processing device such as dialyzer 76 (FIG. 10). Connector 78 may be a connector that complies with DIN standards in a conventional manner.

As shown in FIG. 11, male luer connector 106 may be carried on the end of pressure tubing 42a in a manner similar to tubing 42 of FIG. 1, except that pressure tubing 42a is not shown permanently bonded to pod 80. Thus, pod 80 may be reversibly or permanently attached to a connector 41 (FIG. 1) which communicates with an electronic pressure monitor 43 of the machine. In this present embodiment of FIGS. 10 and 11, tubing 42a, end connector 44a, and male luer connector 106, having locking sleeve 108, may be reusable for a large number of connections with different pressure sensing pods 80, since connector 116 communicates with volume 92 inside of pressure sensing pod 80, which volume is sealed from the blood flow path 31a, by diaphragm 26a. Thus, sterility does not have to be an attribute of pressure tubing 42a. This permits the long term or even permanent communication of tubing 42a and electronic pressure sensing device 43, wherever remotely located on the machine, and its sequential use with a large number of separate blood flow sets, such as that of FIG. 7.

Saline line 69 of set 60 provides a connection with pressure chamber or pod 68 in a manner similar to the saline line connection 34 of FIG. 2. Pressure sensing pod 68 also carries a connector 116a similar in structure and function to connector 116.

The particular design of partition 120 and sealed connector 116 and other disclosed designs, may be used in other modes of use for medical fluid flow sets, for example, as a sealed port for a Y or T connector, or a connector to another kind of pod or chamber for any of various uses. The connectors disclosed may be connected to a pump tubing segment connector 72 to receive a heparin branch line (not shown), and/or the connectors may be carried on arterial inlet connectors to receive an attachable injection site. In this way, branch tubing components of the blood set can be reduced or eliminated, for cost savings.

Referring to FIGS. 12-17, a diaphragm chamber or pod 80a is similar to chamber 80 except as otherwise described. Pod 80a carries a sealed port 116a, similar to port 116, attached to pod 80a, and generally of the design of a female luer lock connector, having lugs or screw threads 118a in conventional manner or other sealing and/or locking means. Port 116a is sealed by partition 120a, so that the volume 92a which is spaced by the diaphragm of pod 80a (similar to diaphragm 28a in the previous embodiment) is hermetically sealed when the periphery of pod 80a is sealed, as in the previous embodiment. Partition 120a has a peripheral connection with the lumen-defining wall 96a of port 116a.

Figure 12:
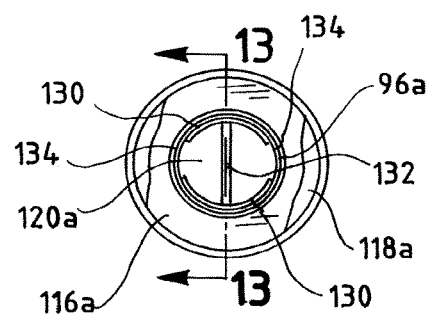
FIG. 12 is a view similar to FIG. 9 of another embodiment of the sealed port partition
Figure 13:
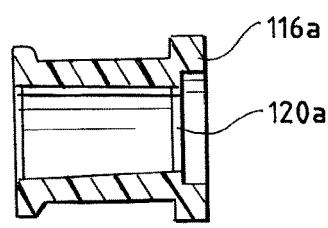
FIG. 13 is a sectional view taken along line 13-13 of FIG. 12.
Figure 14:
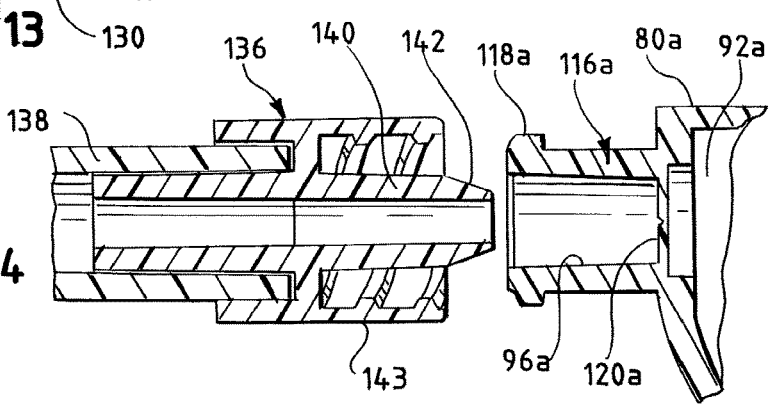
FIG. 14 is a fragmentary view of the sealed port of FIG. 13, carried on a pod as in previous embodiments, about to be connected with a pressure tube as in previous embodiments.
Figure 15:
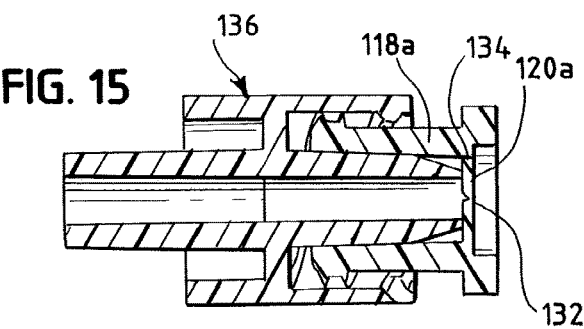
FIG. 15 is a sectional view showing an initial connection (of luer lock type) of the components of FIG. 14.
Figure 17:
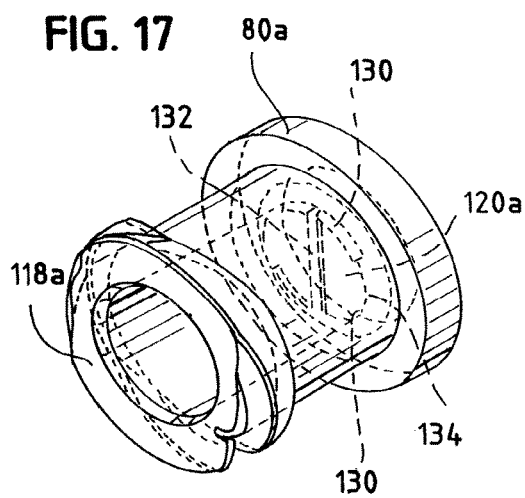
FIG. 17 is a perspective view of the connector of FIG. 14, showing internal parts.
Figure 16:
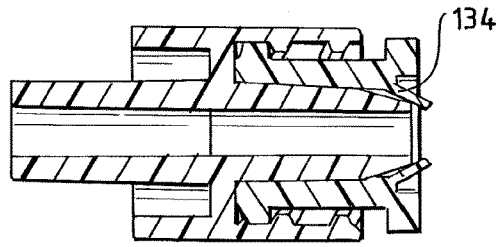
FIG. 16 shows a fully advanced, sealed connection of the components of FIG. 14, with the partition of FIG. 12 being opened by advancement of the male luer lock connector.

As shown particularly in FIG. 12, partition 120a has 360 degree peripheral connection with lumen wall 96a, with a diametrically opposed pair of peripheral, thin walled tear lines 130, being positioned adjacent to lumen wall 96a and comprising a major portion of the circumference of partition 120a. These tear lines are relatively thin, comprising lines partition wall of material typically about 0.2-0.4 mm thick, depending of course upon the particular plastic used. These thin, frangible peripheral tear lines may extend, for example, at least about 250 degrees of the total circumference, and typically no more than about 340 degrees.

Partition 120a also defines a similarly thin-walled tear line 132 extending substantially as a diameter across partition 120a, to generally bisect partition 120a by separating it into two, generally similar halves.

At the periphery of the remaining portions of the circumference of partition 120a, minor portions of the periphery 134, which are the remaining portions of the circumference, may be thicker than portions 130 and 132, being generally on the order of 1 mm thick or more, so as not to be frangible, but, rather, to serve as hinges to respectively permit the two halves of partition 120a on either side of central, thin tear line 132 to pivot as partition 120a is broken open by the pressure of an advancing tubular member such as male connector 136, which may be connected to pressure connection tubing 138, for similar purpose as tubing 42, 42a, or for any other desired medical purpose.

Connector 136 may define a projecting, frustoconical sealing member 140 which mates in the manner of a luer connector with tapered, frustoconical lumen wall 96a. Projecting member 140 further carries a partition opening member 142 at its forward end, which, in turn, may comprise a frustoconical member of greater wall angle to the axis of connector 136, or it may comprise a pointed member with open lumen flow ports positioned beside it, or any member which can press against partition 120a to rupture lines 130, 132, to open partition 120a.

Thus, instead of a thickened partition broken by a regular male luer or other tube having a flush end, as in the previous embodiment, in this embodiment, a partition is provided without thick sections (but having the thinned tear lines 130, 132) and which uses an extension 142 on a male connector 140 to break partition 120a. This has advantage when one does not want a regular male luer lock connector or the like to mistakenly access the device, since it can be formed so that a male connector engages and seals with frustoconical lumen surface 96a before the male luer can reach partition 120a to press it, to cause possible premature opening. Thus, a special set with a special connector 136 may be required to open sealed port 116a.

This special male connector 136 is carried on the end of pressure tubing 138, which may be similar to pressure tubing 42a of FIG. 10, except that pressure tubing 138 is not permanently bonded to pod 80a and upper compartment portion 92a, and may be reversibly or permanently attached to a pressure port similar to port 41, which communicates with an electronic pressure monitor 43 of a pressure measuring machine.

In the embodiment of FIGS. 12-17, tubing 138 and special male connector 136, having locking sleeve 143, may be reusable for a large number of connections with different diaphragmatic chambers or pods 80a, since connector 116a is sealed from the blood flow path by its diaphragm. Sterility thus does not have to be an attribute of pressure tubing 138 (or tubing 42a), permitting the long term and even permanent connection of tubing 138 to electronic pressure sensing system 41, 43, wherever remotely located on the machine, such as a dialysis machine. Thus, a significant economy may be achieved by the sequential use of tubing 138 and connector 136 with a large number of separate blood flow sets.

Figure 18:
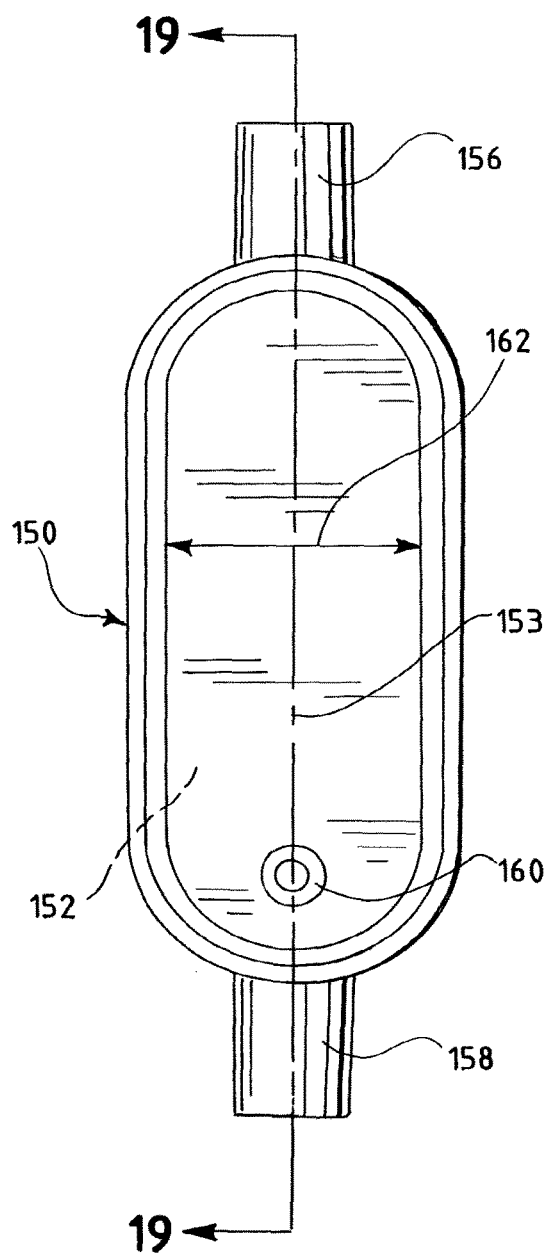
FIG. 18 is a plan view of another embodiment of the pod of this invention.
Figure 19:
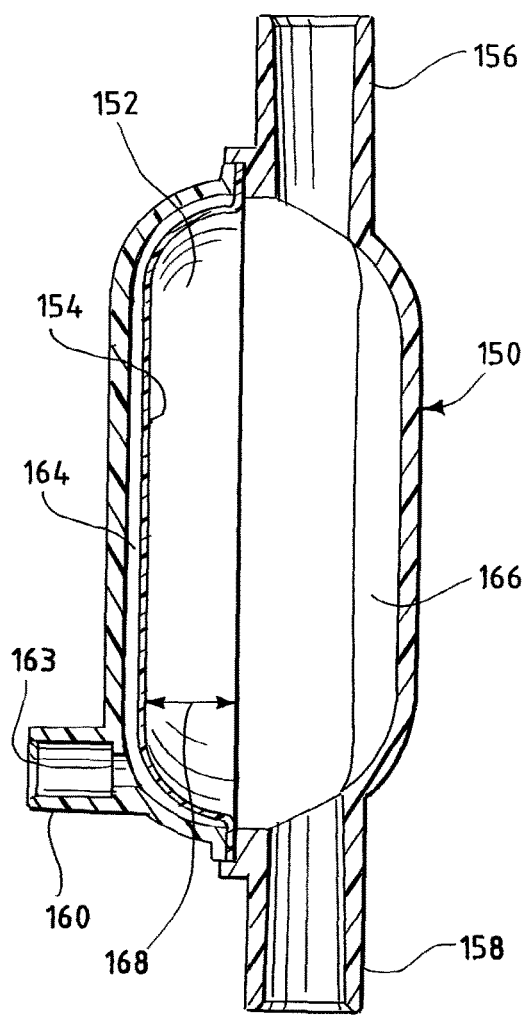
FIG. 19 is a sectional view taken along line 18-18 of Fig. A.

Referring to FIGS. 18 and 19, a pod 150, defining a chamber 152 and a flexible diaphragm 154, defining a dome in a manner similar to those of previous embodiments such as diaphragm 26, is disclosed. Pod 150 may be used in a manner described with respect to pods of the previous embodiments, being connected through tubular connectors 156, 158 to tubular components of an extracorporeal blood set, or directly connected at one of the connectors 156, 158 to a dialyzer or the like, as previously described. Port 160 is provided, being for a similar purpose as is port 116, 116a of the previous embodiment, carrying a partition 163, which may be of design similar to the partitions of the previous embodiments and for similar purpose.

It can be seen that pod 150 is elongated, and in some embodiments of this invention, the length of pod chamber 152 along its longest axis 153 may be at least twice its width 162. This provides a greater volume to pod 150 compared with a round pod having a diameter similar to the width 162 of pod 150. The dome of diaphragm 154 can flip back and forth in a manner described with respect to previous embodiments, and thus, the overall volume of the air side 164 of the chamber and go from essentially zero as shown in FIG. 19 to a volume which is at least 2.5 cc, preferably 3.0 cc., and specifically more than 3.2 cc., typically, so that an air volume of that amount can form when flexible diaphragm 154 is displaced to its maximum position on the right of FIG. 19, to minimize the volume of blood compartment 166 in pod 150, for the advantages previously discussed.

Thus, as flexible diaphragm 154 flips its dome between its two positions, there is a volume displacement, displacing at least 2.5 cc. of air and typically greater amounts as specified above. This amount of displacement assures that a broad pressure range in pod 150 can be monitored despite using a lengthy tube several feet in length which connects port 160 with a pressure transducer mounted within a pressure sensing component of, for example, an extracorporeal blood processing machine, as in previous embodiments. Specifically, it is desirable for the system to be able to register a range of 500 mmHg of positive pressure to minus 250 mmHg of reduced or negative pressure without the dome of diaphragm 154 coming into contact with a wall of pod 150 so that it can no longer move its position responsive to pressure change. It can also be seen that stretching of the elastomer of diaphragm 154 is minimized by the dome configuration as the dome moves back and forth. In fact, in some embodiments, flexible but non elastomeric materials may be used for the dome 154.

Specifically, to achieve the desired volumes in a small pod, the width 162 of diaphragm 154 (essentially the same as the chamber width) should be at least twice the depth 168 of the dome of diaphragm 154 and in some embodiments the width 162 should be at least three times the depth 168 of dome 164. This helps to provide a blood flow path, having a maximum thickness which is not too deep, causing a risk of blood stagnation and clotting, while at the same time providing an adequate amount of air displacement on the air side of diaphragm 154 so that a wide range of pressures can be measured.

The above has been offered for illustrative purposes only, and is not intended to limit the scope of the invention of this application, which is as defined in the claims below.

The invention claimed is:

1. A tubular blood flow set which comprises:
   a pressure sensing pod defining a chamber, said pod being connected in flow-through relation to blood flow tubing of said set, said set defining a length of pressure tubing connectable at one end with said chamber via a pressure port thereof, for connection at the other pressure tubing end with a pressure measuring equipment connector with said pod being spaced from said connector; and
   a flexible diaphragm sealingly mounted within said pod between connections of said blood flow tubing and said pressure tubing, said diaphragm being moveable between first and second positions, the diaphragm in said first position bowing outwardly to substantially maximize volume in said chamber that communicates with said blood flow tubing, the diaphragm in said second position bowing inwardly to substantially minimize but not eliminate the blood volume in said chamber that is inside of said diaphragm, said diaphragm in use being in contact on one side thereof with flowing blood;
   the pressure port being in communication with said chamber on a side of said diaphragm opposite said connections of said blood flow tubing;
   the pod being provided, prior to use, with said diaphragm in a desired one of the first and second positions by means of:
   said diaphragm having a central dome portion that can flip between said first position said second position; and
   said pressure port having a seal therein that keeps the diaphragm in said desired one of said first and second positions until connection with a pressure measuring device causes said seal to open.

2. The set of claim 1, wherein the pod is provided, prior to use, in one of the first and second positions by means of said diaphragm having a central dome portion that can flip between said first position said second position.

3. The set of claim 2, wherein the length of pressure tubing permanently connected said one end with said chamber via said pressure port.

4. The set of claim 2, wherein the dome portion has a continuous curved cross-section.

5. The set of claim 1, wherein the pod is provided, prior to use, in one of the first and second positions by means of said pressure port having a seal therein the keeps the diaphragm in a desired one of said first and second positions until connection with a pressure measuring device causes said seal to open.

6. The set of claim 5, wherein the pressure tubing is unconnected to the pressure port.

7. The set of claim 6, wherein the pressure tubing has a connector connectable to said pressure port, said connector containing a member that breaks said seal.

* * * * *